United States Patent
Volkman et al.

(10) Patent No.: US 10,738,095 B2
(45) Date of Patent: Aug. 11, 2020

(54) ENGINEERED CCL20 LOCKED DIMER POLYPEPTIDE

(71) Applicant: THE MEDICAL COLLEGE OF WISCONSIN, INC., Milwaukee, WI (US)

(72) Inventors: Brian F. Volkman, Muskego, WI (US); Anthony E. Getschman, Wauwatosa, WI (US); Sam T. Hwang, Brookfield, WI (US); Yasutomo Imai, Milwaukee, WI (US); Francis C. Peterson, Racine, WI (US)

(73) Assignee: The Medical College of Wisconsin, Inc., Milwaukee, WI (US)

(*) Notice: Subject to any disclaimer, the term of this patent is extended or adjusted under 35 U.S.C. 154(b) by 0 days.

(21) Appl. No.: 15/579,114

(22) PCT Filed: May 31, 2016

(86) PCT No.: PCT/US2016/034956
§ 371 (c)(1),
(2) Date: Dec. 1, 2017

(87) PCT Pub. No.: WO2016/196429
PCT Pub. Date: Dec. 8, 2016

(65) Prior Publication Data
US 2018/0237486 A1    Aug. 23, 2018

Related U.S. Application Data

(60) Provisional application No. 62/170,347, filed on Jun. 3, 2015.

(51) Int. Cl.
*C07K 14/52* (2006.01)
*A61K 38/00* (2006.01)

(52) U.S. Cl.
CPC ............ *C07K 14/521* (2013.01); *A61K 38/00* (2013.01)

(58) Field of Classification Search
None
See application file for complete search history.

(56) References Cited

U.S. PATENT DOCUMENTS

| 4,160,452 A | 7/1979 | Theeuwes |
| 4,256,108 A | 3/1981 | Theeuwes |
| 4,265,874 A | 5/1981 | Bonsen et al. |
| 5,288,931 A * | 2/1994 | Chang .................. C07K 1/1133 435/69.1 |
| 7,112,660 B1 * | 9/2006 | Domingues ........ C07K 14/5406 424/85.2 |
| 2002/0004041 A1 | 1/2002 | Albert et al. |
| 2002/0061599 A1 | 5/2002 | Elling et al. |
| 2002/0102234 A1 | 8/2002 | Debets et al. |
| 2002/0138860 A1 | 9/2002 | Cook et al. |
| 2002/0147312 A1 | 10/2002 | O'Keefe et al. |
| 2003/0017979 A1 | 1/2003 | Mack et al. |
| 2003/0045474 A1 * | 3/2003 | Sailer ................. A61K 38/1875 514/8.8 |
| 2003/0077247 A1 | 4/2003 | Caux et al. |
| 2003/0124628 A1 | 7/2003 | Burns et al. |
| 2003/0140361 A1 | 7/2003 | Brennan et al. |
| 2003/0207287 A1 | 11/2003 | Short |
| 2003/0215421 A1 | 11/2003 | McDonald et al. |
| 2004/0001803 A1 | 1/2004 | Hancock et al. |
| 2004/0018563 A1 | 1/2004 | Burns et al. |
| 2004/0023286 A1 | 2/2004 | Wei |
| 2004/0042998 A1 | 3/2004 | Oldham et al. |
| 2004/0161425 A1 | 8/2004 | Munn et al. |
| 2004/0197329 A1 | 10/2004 | Nakayama et al. |
| 2005/0064464 A1 | 3/2005 | Punnonen et al. |
| 2005/0148029 A1 | 7/2005 | Buechler et al. |
| 2005/0164222 A1 | 7/2005 | Punnonen et al. |
| 2005/0191702 A1 | 9/2005 | Mack et al. |
| 2005/0222069 A1 | 10/2005 | Punnonen et al. |
| 2005/0287142 A1 | 12/2005 | Nakayama et al. |
| 2006/0088510 A1 | 4/2006 | Lee et al. |
| 2006/0194287 A1 | 8/2006 | Girard et al. |
| 2006/0198820 A1 | 9/2006 | McDonald et al. |
| 2006/0240016 A1 | 10/2006 | Aguilar et al. |
| 2006/0275295 A1 | 12/2006 | Jullien et al. |
| 2007/0087373 A1 | 4/2007 | Punnonen et al. |
| 2007/0154487 A1 | 7/2007 | Littman et al. |
| 2007/0166280 A1 | 7/2007 | Caux et al. |
| 2007/0212733 A1 | 9/2007 | Martin |
| 2008/0214451 A1 | 9/2008 | Kuliopulos et al. |
| 2009/0092578 A1 | 4/2009 | Su et al. |
| 2009/0305984 A1 * | 12/2009 | Volkman .............. C07K 14/522 514/1.1 |
| 2011/0091410 A1 | 4/2011 | Volkman et al. |
| 2011/0097303 A1 | 4/2011 | Zasloff |
| 2011/0110852 A1 | 5/2011 | Miller et al. |
| 2011/0293607 A1 | 12/2011 | Labrijn et al. |
| 2012/0129820 A1 | 5/2012 | Seither et al. |
| 2012/0148592 A1 | 6/2012 | Imai et al. |

(Continued)

OTHER PUBLICATIONS

Tokuriki et al., 2009, Curr. Opin. Struc. Biol. 19:596-604).*
Bhattacharya et al. (2017, PLoS ONE 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Harper, et al., Th17 Cytokines Stimulate CCL20 Expression in Keratinocytes in Vitro and In Vivo: Implications for Psoriasis Pathogenesis, Journal of Investigative Dermatology, 2009; 129(9): 2175-2183.

(Continued)

*Primary Examiner* — Elizabeth C. Kemmerer
(74) *Attorney, Agent, or Firm* — Quarles & Brady LLP

(57) ABSTRACT

The present invention provides a CCL20 locked dimer polypeptide, pharmaceutical compositions thereof, and methods of using said dimer in the treatment of psoriasis, inflammatory disorders and autoimmune disease.

4 Claims, 5 Drawing Sheets
Specification includes a Sequence Listing.

(56) References Cited

U.S. PATENT DOCUMENTS

| | | |
|---|---|---|
| 2012/0201746 A1 | 8/2012 | Liu et al. |
| 2012/0208769 A1 | 8/2012 | Nelson et al. |
| 2012/0251541 A1 | 10/2012 | Baurin et al. |
| 2012/0258126 A1 | 10/2012 | Scholler et al. |
| 2012/0263764 A1 | 10/2012 | Watson |
| 2012/0269765 A1 | 10/2012 | Garcia et al. |
| 2014/0011238 A1 | 1/2014 | Baurin et al. |
| 2014/0045215 A1 | 2/2014 | Imai et al. |
| 2014/0056895 A1 | 2/2014 | Baurin et al. |
| 2014/0154252 A1 | 6/2014 | Thompson et al. |
| 2014/0154743 A1* | 6/2014 | Levy ............... C07K 14/245 435/69.6 |
| 2014/0205653 A1 | 7/2014 | Dubensky et al. |
| 2015/0004167 A1 | 1/2015 | Wu et al. |

OTHER PUBLICATIONS

Joshua, et al., Design and Receptor Interactions of Obligate Dimeric Mutant of Chemokine Monocyte Chemoattractant Protein-1 (MCP-1), Journal of Biological Chemistry, 2012; 287(18): 14692-14702.
Getschman, et al., Protein engineering of the chemokine CCL20 prevents psoriasisform dermatitis oin an IL-23-dependent murine model, Proceedings of the National Academy of Sciences of the United States of America, 2017; 114(47): 12460-12465.
The International Search Report and Written Opinion for International Patent Application No. PCT/US2016/034956 dated Sep. 2, 2016.
Chan, D. et al., Human Macrophage Inflammatory Protein 3 alpha: Protein and Peptide Nuclear Magnetic Resonance Solution Structures, Dimerization, Dynamics, and Anti-Infective Properties., Antimicrobial Agents and Chemotherapy, Mar. 2008; vol. 52, No. 3: pp. 883-894; p. 883, col. 2, paragraph 2; p. 887, col. 1, paragraph 2; p. 888, col. 2, paragraph 1; p. 892, col. 1, paragraph 2.
Hoover, D.M. et al., The Structure of Human Macrophage Inflammatory Protein-3 alpha/CC:20., Linking Antimicrobial and CC Chemokine Receptor-6-Binding Activities with Human Beta-Defensins. The Journal of Biological Chemistry., Jul. 30, 2002; pp. 37647-37654; whole document.
Hromas, R. et al., Cloning and Characterization of Exodus, a Novel beta-Chemokine. Blood. May 1, 1997, vol. 89, No. 9; pp. 3315-3322; whole document; Supplemental document: CC motif chemokine 20 isoform 1 precursor [*Homo sapiens*]. National Center for Biotechnology Information. Genbank Entry Accession No. NP_004582. May 1, 1997 [retreived on Aug. 9, 2016]. Retrieved from the Internet: <URL: http://www.ncbi.nlm.nih.gov/protein/4759076/>; pp. 1-3.
Aramori, I. et al. 1997. The EMBO journal. 16: 4606-4616.
Baba, M. et al. 1997. The Journal of biological chemistry. 272:14893-14898.
Baly, D.L. et al. 1998. Journal of immunology. 161: 4944-4949.
Blanpain, C. et al. 2003. The Journal of biological chemistry. 278: 5179-5187.
Campanella, G.S. et al. 2006. Journal of immunology. 177:6991-6998.
Chan, D.I. et al. 2008. Antimicrobial agents and chemotherapy. 52:883-894.
Cohn et al., 1997, J. Exp. Med. 186,1737-1747.
Crump, M.P. et al. 1997. The EMBO journal. 16:6996-7007.
Dombkowski, A.A. 2003. Bioinformatics. 19:1852-1853.
Drury, L.J. et al. 2011. Proc. of the Natl Acad. of Sciences. 108:17655-17660.
Girardi, M. 2006. The Journal of investigative dermatology. 126:25-31.
Hansra P. et al., "Carrageenan-Induced Arthritis in the Rat," Inflammation, 24(2): 141-155, (2000).
Hassan, S. et al. 2011. Int. J. of cancer. Journal international du cancer. 129:225-232.
Hedrick, M.N. et al. 2009. The Journal of clinical investigation. 119:2317-2329.
Homey, B. et al. 2000. J. of immunology. 164:6621-6632.
Hoover, D.M. et al. 2002. The Journal of biological chemistry. 277:37647-37654.
Jansma, A. et al. 2009. Chapter 2. Homo- and Hetero-Oligomerization of Chemokines Methods in enzymology. 461:31-50.
Kagami, S. et al. 2010. The Journal of investigative dermatology. 130:1373-1383.
Kufareva, I. et al. 2014. Proc. Natl Academy of Sciences. 111:E5363-5372.
Kurd, S.K. et al. 2009. J.American Academy of Dermatology. 60:218-224.
Laggner, U et al. 2011. Journal of immunology. 187:2783-2793.
Langley, R.G. et al. 2014. The New England journal of medicine. 371:326-338.
Liao, F. et al. 1999. Journal of immunology. 162:186-194.
Mabuchi, T. et al. 2011. Journal of immunology. 187:5026-5031.
Malik, Z.A. et al. 2006. Acta crystallographica. 62:631-634.
Proudfoot, A.E. et al. 2003. PNAS. 100:1885-1890.
Ravindran, A. et al. 2013. The Journal of biological chemistry. 288:12244-12252.
Rodriguez-Frade, J.M. et al. 1999. The Journal of cell biology. 144:755-765.
Rosenkilde, M.M. et al. 2004. The Journal of biological chemistry. 279:3033-3041.
Rosenkilde, M.M. et al. 2006. The Journal of biological chemistry. 281: 13199-13208.
Sierro, A. et al. 2001. PNAS 98(24): 13722-13727.
Sutton, C.E et al. 2009. Immunity. 31:331-341.
Takekoshi, T et al. 2012. Molecular cancer therapeutics. 11:2516-2525.
Tan, J.H et al. 2012. The Journal of biological chemistry. 287:14692-14702.
Tan, J.H., et al. 2013. The Journal of biological chemistry. 288:10024-10034.
Veldkamp, C.T. et al. 2008. Sci Signal. 1(37):ra4.
Winter C. A. et al., "Carrageenan-Induced Edema in Hind Paw of the Rat as an Assay for Anti-inflammatory Drugs" Proc. Soc. Exp. Biol Med. 111, 544-547, (1962).
Wirtz, S. et al., "Chemically induced mouse models of intestinal inflammations" Nature Protocols 2, 541-546, (2007).
Zidar, D.A. et al. 2009. Proceedings of the National Academy of Sciences. 106:9649-9654.
Nasser, M.W., et al. 2009. Differential activation and regulation of CXCR1 and CXCR2 by CXCL8 monomer and dimer. Journal of immunology. 183:3425-3432.
Poluri, K.M., et al. 2013. Molecular basis of glycosaminoglycan heparin binding to the chemokine CXCL1 dimer. The Journal of biological chemistry. 288:25143-25153.

* cited by examiner

Figures 1A-F
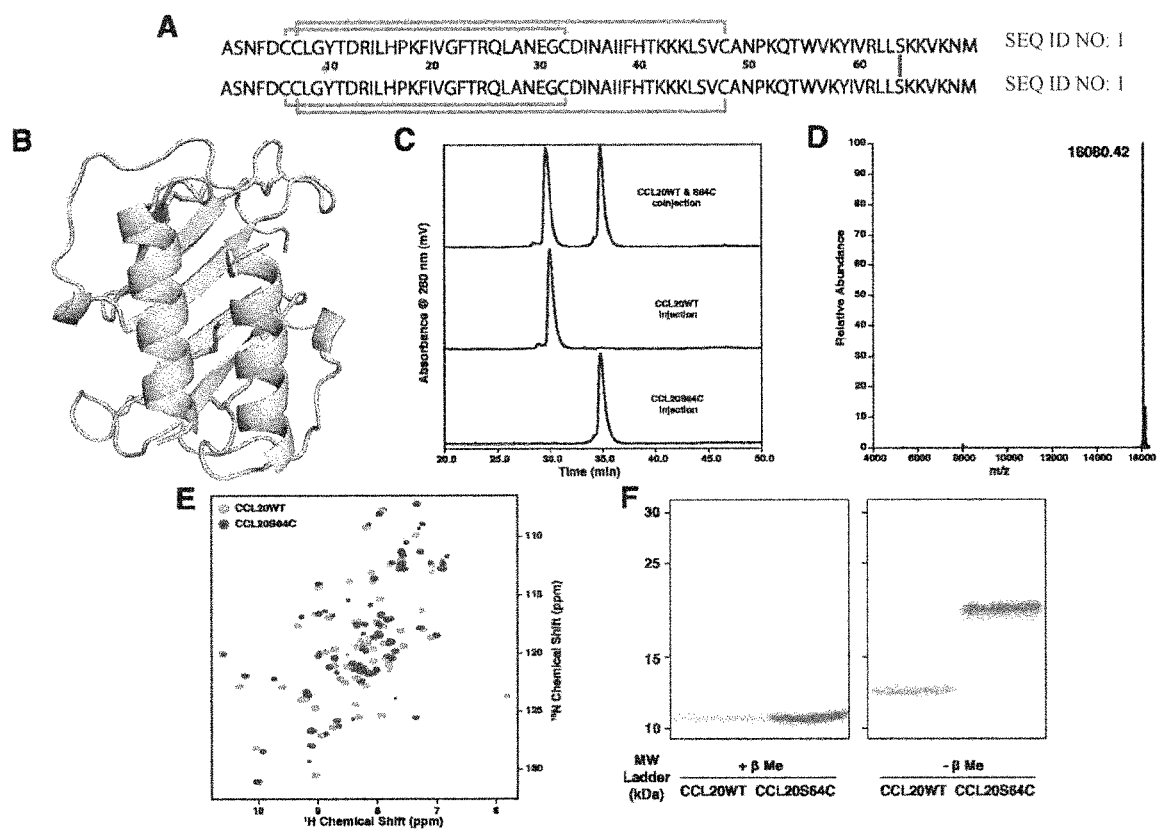

Figures 2A-E
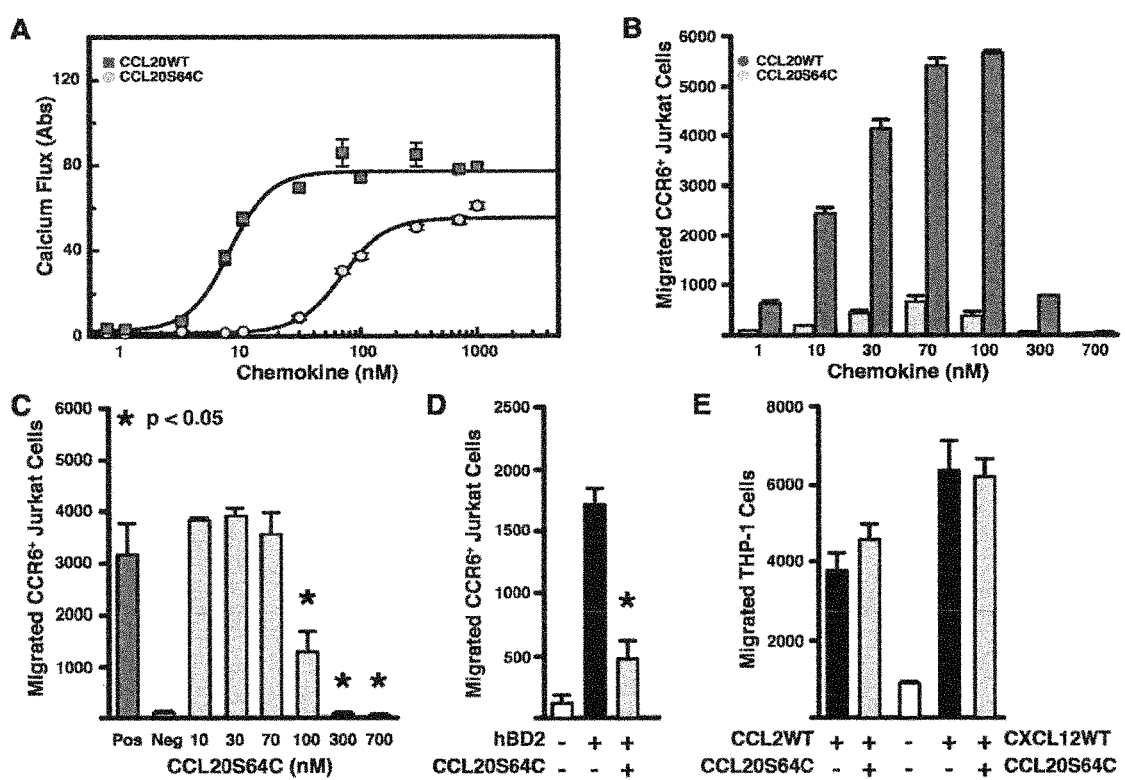

Figures 3A-F
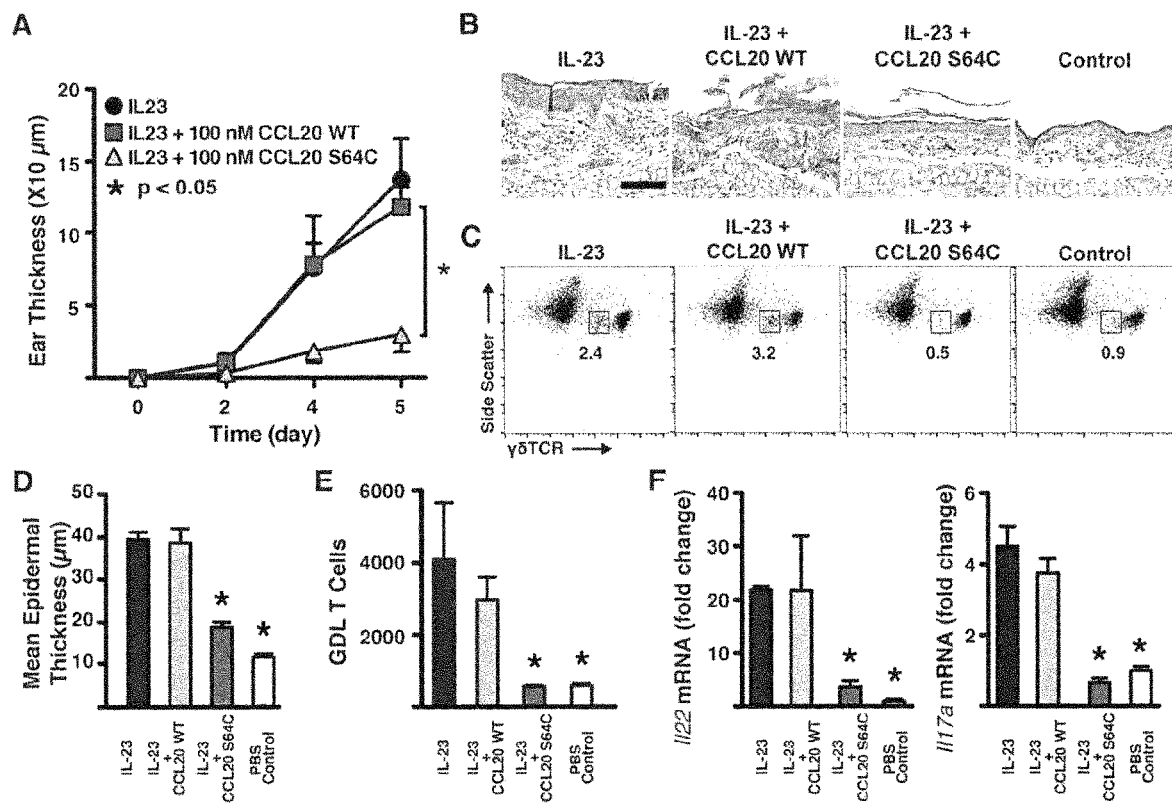

Figures 4A-D
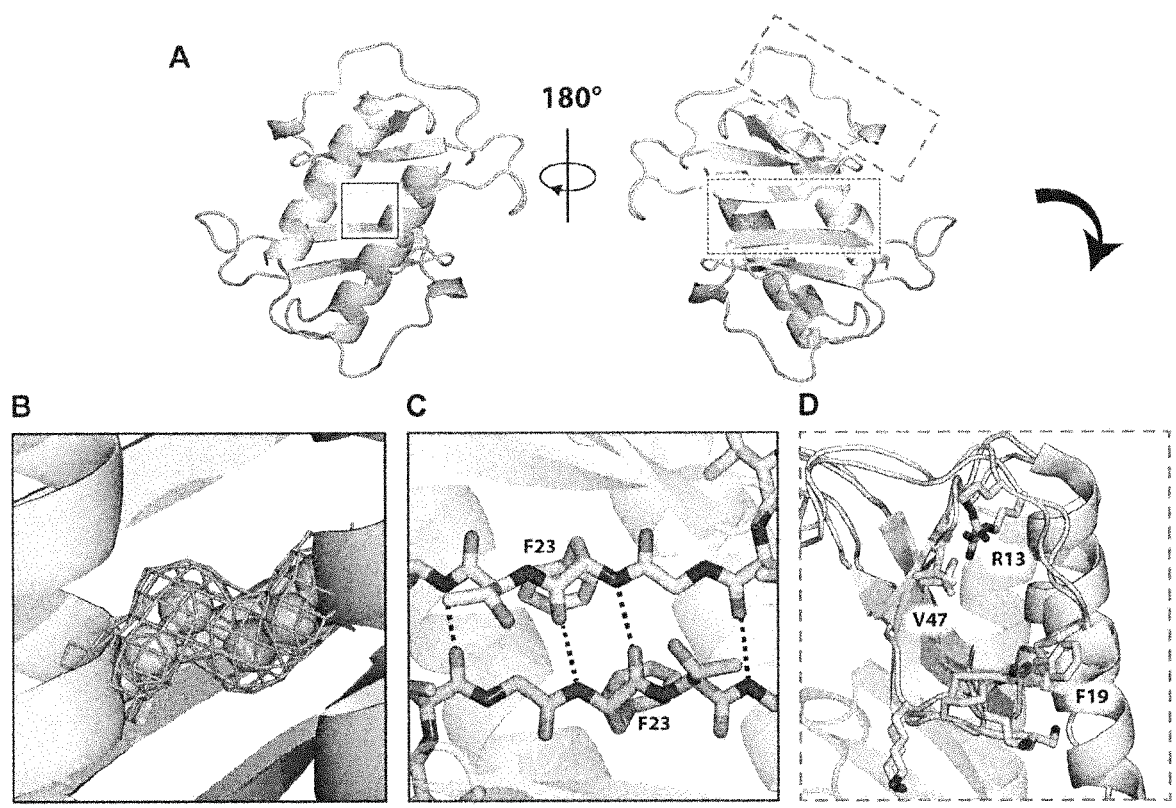

Figures 5A-E
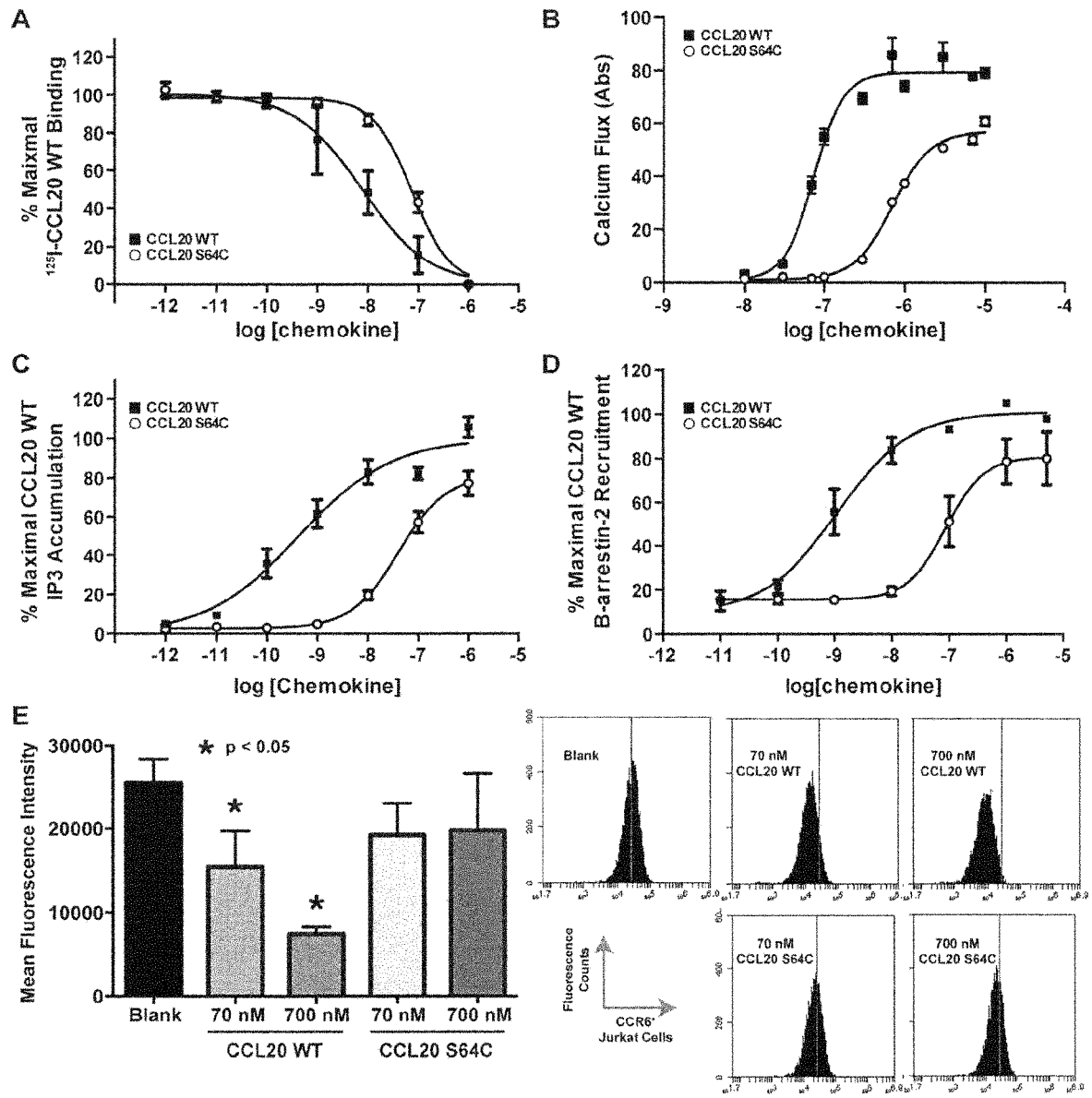

ENGINEERED CCL20 LOCKED DIMER POLYPEPTIDE

CROSS-REFERENCE TO RELATED APPLICATIONS

This application represents the national stage entry of PCT International Application No. PCT/US2016/034956 filed on May 31, 2016 and claims priority to U.S. Provisional Patent Application No. 62/170,347, filed Jun. 3, 2015, the contents of which are incorporated by reference in its entirety.

STATEMENT REGARDING FEDERALLY SPONSORED RESEARCH OR DEVELOPMENT

This invention was made with government support under AI058072 awarded by the National Institute of Health. The government has certain rights in the invention.

FIELD OF THE INVENTION

The invention relates generally to a novel CCL20 locked dimer polypeptide, pharmaceutical compositions thereof, and methods of using the CCL20 locked dimer in the treatment of psoriasis and other autoimmune and inflammatory diseases.

BACKGROUND

Chemokines are a superfamily of chemoattractant cytokine proteins which primarily serve to regulate a variety of biological responses and promote the recruitment and migration of multiple lineages of leukocytes and lymphocytes to a body organ tissue. Chemokines are classified into four families according to the relative position of the first two cysteine residues in the protein. In one family, the first two cysteines are separated by one amino acid residue (the CXC chemokines) and in another family the first two cysteines are adjacent (the CC chemokines). In a third family, the first two cysteines are separated by three amino acids ($CX_3C$ chemokines). In a fourth family there is only one cysteine in the amino terminus (C chemokines).

The chemokine-receptor pair of CCL20/CCR6 regulates dendritic and T cell trafficking to sites of injury or infection through the establishment of concentration gradients in vivo (Liao et al., 1999). During the general inflammatory response, the ~8 kDa chemokine is secreted by lymphoid cells into the extracellular matrix where it binds and activates its single, seven transmembrane G protein-coupled receptor (GPCR), CCR6 expressed on the surface of migratory cells (Baba et al., 1997).

Psoriasis is a chronic inflammatory skin disease affecting 2-3% of the global population (Kurd and Gelfand, 2009) characterized by the infiltration of Th17 cells to the skin in response to injury or autoantigens. T cells, including those with low expression of the gamma-delta T cell receptor, are recruited to the dermis and epidermis by a number of chemokines, including CCL20. Together with its receptor CCR6, CCL20 plays a critical role in the development of psoriasiform dermatitis in mouse models.

Current psoriasis treatments that target Th17 pathway cytokines and tumor necrosis factor-a (TNF-a) can be highly effective in treating humans with psoriasis (Langley et al., 2014). However, a neutralizing anti-CCL20 monoclonal antibody reduced psoriasis-like inflammation, suggesting that inhibition of CCL20/CCR6-mediated T cell recruitment may also be a useful therapeutic strategy (Mabuchi et al., 2011).

Chemokines engage their receptors via an extensive protein-protein interface that encompasses domains at the extracellular surface and a deep pocket within the transmembrane domain (the orthosteric site) that is occupied by the chemokine N-terminus (Kufareva et al., 2014). Native chemokines are typically full, balanced GPCR agonists that elicit characteristic cellular responses, including the release of intracellular calcium from the endoplasmic reticulum and cell migration. Chemokine receptor antagonists, such as small molecules, peptides or mutated chemokines, typically block GPCR signaling by preventing activation at the orthosteric site (Crump et al., 1997; Hassan et al., 2011; Rosenkilde et al., 2004).

Partial or biased agonists of chemokine receptors are characterized by a selective loss of efficacy, such as AOP-Rantes, which induces CCR5-mediated calcium signaling but lacks pro-migratory signaling and has altered receptor recycling (Rodriguez-Frade et al., 1999). Additionally, Zadir and colleagues showed that biased agonism of CCR7 by its two chemokine ligands, CCL21 and CCL19, results in differing patterns of GPCR kinase recruitment but no difference in $G_{i/o}$ signaling (Zidar et al., 2009). While N-terminal modifications can alter the pharmacologic properties of a chemokine by disrupting orthosteric site contacts, manipulation of the chemokine oligomeric state can also change its signaling profile in potentially useful ways.

Chemokines typically bind and activate their cognate GPCRs in the monomeric state, but self-association is important for binding to cell surface glycosaminoglycans and thus for in vivo chemokine function (Campanella et al., 2006). Members of the CXC and CC chemokine subfamilies generally adopt distinct quaternary structures that utilize either the $\beta 1$ strand (CXC) or residues near the N-terminus (CC) for the dimer interface (Jansma et al., 2009). Changes in the oligomeric state of a chemokine can alter receptor binding, activation and downstream signaling. Dimerization of most CC chemokines occludes key receptor binding epitopes, rendering them nonfunctional as GPCR ligands (Tan et al., 2013). Some CXC chemokines, however, that have been modified to be constitutively dimeric are competent to bind their receptors and can function as partial agonists and inhibitors (Veldkamp et al., 2008). Among CC chemokines for which structures have been solved, CCL20 is unique in that it adopted a CXC-type dimer in two high-resolution crystal structures with no evidence for the canonical CC dimer (Hoover et al., 2002; Malik and Tack, 2006).

Accordingly, there is a current need for cost-effective pharmaceutical agents and treatment methods for treating psoriasis and other autoimmune or inflammation disorders.

SUMMARY OF THE INVENTION

The inventors have engineered a novel CCL20 locked dimer polypeptide comprising two monomers linked together. The dimer is useful in treating various conditions including cancer, autoimmune disorders and inflammation disorders.

In one preferred embodiment the dimer comprises two monomers bound together, wherein at least one monomer has the amino acid sequence as shown in SEQ ID NO:1 (ASNFDCCLGYTDRILHPKFIVGFTRQLANEGCDI-NAIIFHTKKKLSVCANPKQTWVKYIVRL LCKK-VKNM). The CCL20WT sequence is publicly available.

In another embodiment, the present invention provides a composition comprising a CCL20 locked dimer polypeptide and a pharmaceutically acceptable carrier or diluent.

In another embodiment, the present invention provides an isolated CCL20 locked dimer polypeptide, wherein the dimer preferably consists of at least one monomer having the amino acid sequence as shown in SEQ ID NO:1.

In another embodiment, the present invention provides a method of treating psoriasis in a subject having or at risk of having psoriasis, the method comprising administering to the subject a therapeutically effective amount of a composition comprising a CCL20 locked dimer.

In another embodiment, the present invention provides a method of treating an autoimmune disease in a subject having or at risk of having an autoimmune disease, the method comprising administering to the subject a therapeutically effective amount of a composition comprising a CCL20 locked dimer polypeptide.

In another embodiment, the present invention provides a method of treating an inflammatory disorder in a subject having or at risk of having an inflammatory disorder, the method comprising administering to the subject a therapeutically effective amount of a composition comprising a CCL20 locked dimer polypeptide.

In another embodiment, the present invention provides a kit comprising a CCL20 locked dimer polypeptide wherein the dimer preferably comprises at least one monomer having the amino acid sequence as shown in SEQ ID NO:1, a pharmaceutically acceptable carrier or diluent, and instructional material.

BRIEF DESCRIPTION OF THE FIGURES

FIG. 1A. A disulfide-linked CCL20 is a stably folded dimer. The CCL20 amino acid sequence with native (cyan) and non-native (red) disulfide bonds highlighted.

FIG. 1B. A model of CCL20S64C showing the CXC (β-strand) dimer conformation and the intermolecular disulfide bond (red) at position 64.

FIG. 1C. CCL20WT and CCL20S64C were co-injected onto a C18 reverse phase HPLC and elution times are separated by ~5 mins.

FIG. 1D. Mass spectrometry analysis of CCL20S64C (Expected Mass=16080.4 kDa).

FIG. 1E. Heteronuclear single quantum coherence spectra overlay of CCL20WT (orange) and CCL20S64C (blue).

FIG. 1F. SDS-PAGE of CCL20WT and CCL20S64C in the presence and absence of a reducing agent, β-mercaptoethanol.

FIG. 2A. CCL20 S64C is a CCR6 specific ligand that blocks CCL20WT and hBD2 dependent cell migration. CCR6$^+$ Jurkat cell calcium flux was measured in response to CCL20WT (EC$_{50}$=76±11 nM) and CCL20S64C (EC$_{50}$=700±72 nM). Data points are the mean±SEM of six replicates on two separate days.

FIG. 2B. CCR6$^+$ Jurkat cell migration measured in response to increasing amounts of CCL20WT (EC$_{50}$~15 nM) and CCL20S64C. Data points are the mean±SEM of four replicates on two separate days.

FIG. 2C. Inhibition of CCR6$^+$ Jurkat cell migration by CCL20S64C in the presence of 30 nM CCL20WT. Data points are the mean±SEM of four replicates on two separate days.

FIG. 2D. Measurement of CCL20 S64C inhibition of hBD2 dependent (100 nM) CCR6$^+$ Jurkat cell migration. Data points are the mean±SEM of four replicates on two separate days.

FIG. 2E. CCL20S64C inhibition of CCL2WT (1 nM) or CXCL12WT (10 nM) dependent THP-1 cell migration. Data points are the mean±SEM of four replicates from two separate days.

FIG. 3A. The CCL20 locked dimer is a preventative therapeutic for IL-23 induced psoriasis. Time-course of ear swelling. Mice were injected every other day with IL-23 alone or co-administered with CCL20WT or CCL20S64C. The values of ear swelling, the differences in ear thickness from day 0 at each time point, are plotted. Data are expressed as means±SEM (n=6). *P<0.05. Similar results were obtained in two independent experiments.

FIG. 3B. Following treatment with IL-23 alone or co-administered with CCL20WT or CCL20S64C for 6 days, skins were sampled and the skin specimens were stained with hematoxylin and eosin. Bar=100 μm. Data are representative of at least three mice. Similar results were obtained in three independent experiments.

FIG. 3C. Epidermal cell suspensions from each mouse ear were stained with mAbs against γδ-TCR for flow cytometry. The numbers indicate the proportion of side scatter$^{med}$γδ$^{low}$ GDL T cells. A representative result is shown. Similar results were obtained in three independent experiments.

FIG. 3D. Total numbers of GDL T cells per ear of each group were counted. Data are expressed as means±SEM (n=3). *P<0.05 vs. IL-23 alone groups. Similar results were obtained in two independent experiments.

FIG. 3E. Epidermal cell suspensions from each mouse ear were processed for RNA extraction for reverse transcriptase-PCR (RT-PCR).

FIG. 3F. Fold changes were calculated for 1117a and 1122 mRNAs normalized for Gapdh mRNA vs. untreated control ear skin. Data are expressed as means±SEM (n=3). *P<0.05 versus IL-23 alone groups. Similar results were obtained in two independent experiments.

FIG. 4A. Crystal structure of CCL20 S64C shows a CXC dimer conformation. Two CCL20 monomers are observed in the asymmetric crystal unit and each α-helix is connected through an intermolecular disulfide bond.

FIG. 4B. Crystal structure showing full electron density (gray mesh) is observed throughout the entire length of the non-native disulfide bond.

FIG. 4C. Crystal Structure showing the backbone peptide interactions stabilize the primary β1-β1 CXC-type dimer interface forming the β-sheet.

FIG. 4D. Crystal structure depicting receptor binding epitopes are structurally conserved between the monomer structure of CCL20 (PDB code: 2JYO) (purple) and the CCL20 locked dimer (wheat).

FIG. 5A. Graph depicting biochemical characterization of CCL20 S64C activation of CCR6. Binding of CCL20 proteins was observed by $^{125}$I-CCL20 WT displacement from CCR6$^+$ transfected COS-7 cells. The K$_d$ value for CCL20 WT and S64C binding to CCR6 was calculated as 7.6 nM and 74.4 nM, respectively, from the corresponding log EC$_{50}$ value of −8.12 [−8.542, −7.698] and −7.128 [−7.245, −7.012].

FIG. 5B. Graph showing administration of CCL20 WT and S64C on CCR6$^+$ Jurkat cells promoted intracellular calcium release with EC$_{50}$ values of 75.0 nM and 715.3 nM, respectively, from the log EC$_{50}$ values of −7.125 [−7.251, −6.999] and −6.145 [−6.234, −6.057].

FIG. 5C. Graph showing accumulation of $^3$H-IP$_3$ was determined by radioactive measurements on transfected CCR6$^+$ COS-7 cells in response to CCL20 WT and S64C with resulting EC$_{50}$ values of 0.4 nM and 41.3 nM, respectively, from the log $EC_{50}$ values of −9.368 [−9.903, −8.833] and −7.384 [−7.625, −7.144].

FIG. 5D. Dose-dependent treatment of U2OS cells with CCL20 WT and S64C promoted β-arrestin-2 recruitment to CCR6 with $EC_{50}$ values of 1.1 nM and 86.2 nM, respectively, from the corresponding log $EC_{50}$ values of −8.954 [−9.349, −8.558] and −7.065 [−7.419, −6.711]. (e) Treatment with CCL20 S64C did not reduce CCR6 cell surface expression (*P<0.05).

FIG. 5E CCR6 internalization in response to CCL20 WT and CCL20 S64C. CCR6 expression at the cell surface of Jurkat cells was quantified by flow cytometry demonstrating treatment with CCL20 S64C concentrations (700 nM) equal to or above the calcium flux and β-arrestin-2 recruitment $EC_{50}$ values showed no significant CCR6 internalization.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only and is not intended to limit the scope of the present invention, which will be limited only by any later-filed nonprovisional applications.

It must be noted that as used herein and in the appended claims, the singular forms "a", "an", and "the" include plural references unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. All publications and patents specifically mentioned herein are incorporated by reference for all purposes including describing and disclosing the materials, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

CCL20 Locked Dimer Polypeptide.

In one embodiment, the invention provides a CCL20 locked dimer polypeptide comprising at least two monomers. The monomers may be identical or may be non-identical. In one embodiment, at least one of the monomers has the amino acid sequence according to SEQ ID NO:1. In alternate embodiments, both monomers have the amino acid sequence according to SEQ ID NO:1.

By "locked" we mean the monomer components of the polypeptide are linked to each other via at least one covalent bond. The terms "locked", "bound", "linked", and "covalently linked" or "covalently bonded" are used interchangeably, and are used to indicate covalent bonding of the monomer components together to form the dimer. A preferred covalent link is a disulfide bond. The monomer and dimer forms do not interconvert. In a preferred embodiment, S64 is replaced with cysteine residues to create at least one symmetrical, intermolecular disulfide bond between opposing α-helices. The terms "locked CCL20 dimer" and "locked CCL20 dimer polypeptide" are used herein interchangeably.

Other residue(s) besides S64 in CCL20 could be mutated to cysteines in order to form the locked dimer similar to the one of the present invention, including, for example, residues V21/T24 (SEQ ID NO: 2), G22/T24 (SEQ ID NO: 3) and F23 (SEQ ID NO:4) at the $1^{st}$ β-strand and V60 (SEQ ID NO:5) and V67 (SEQ ID NO:6) at the α-helix. However, other combinations of residues capable of forming the required non-native disulfide may also be effective.

In some embodiments, the CCL20 dimer comprises at least one monomer having the amino acid sequence as shown in SEQ ID NO:2, SEQ ID NO:3, SEQ ID NO:4, SEQ ID NO:5, or SEQ ID NO:6 or a homologue thereof. In some embodiments, the CCL20 dimer comprises two monomers having the amino acid sequence SEQ ID NO:2 or homologues thereof. In some embodiments, the CCL20 dimer comprises two monomers having the amino acid sequence SEQ ID NO: 3 or homologues thereof. In some embodiments, the CCL20 dimer comprises two monomers having the amino acid sequence SEQ ID NO:4 or homologues thereof. In some embodiments, the CCL20 dimer comprises two monomers having the amino acid sequence SEQ ID NO:5 or homologues thereof. In some embodiments, the CCL20 dimer comprises two monomers having the amino acid sequence SEQ ID NO:6 or homologues thereof.

Additional methods for making locked dimers of CCL20 could also include other types of covalent linkages besides disulfide bonds including, but not limited to, chemical cross-linking reagents.

In a preferred embodiment, the locked dimer of the present invention comprises a substantially pure preparation. By "substantially pure" we mean a preparation in which more than 90%, e.g., 95%, 98% or 99% of the preparation is that of the locked dimer.

In a preferred embodiment, at least one of the monomers comprising the locked dimer of the present invention has the amino acid sequence as shown in SEQ ID NO:1 or a homologue or fragment thereof. In a further preferred embodiment, the dimer comprises two monomers having the amino acid sequence as shown in SEQ ID NO:1 or a homologue or variant thereof. By "homologue" we mean an amino acid sequence generally being at least 80%, preferably at least 90% and more preferably at least 95% homologous to the polypeptide of SEQ ID NO:1 over a region of at least twenty contiguous amino acids. By "fragment," we mean peptides, oligopeptides, polypeptides, proteins and enzymes that comprise a stretch of contiguous amino acid residues, and exhibit substantially a similar, but not necessarily identical, functional activity as the complete sequence. Fragments of SEQ ID NO:1, or their homologues, will generally be at least ten, preferably at least fifteen, amino acids in length, and are also encompassed by the term "a CCL20 monomer" as used herein.

The locked CCL20 dimer could also be incorporated into a larger protein or attached to a fusion protein that may function to increase the half life of the dimer in vivo or be used as a mechanism for time released and/or local delivery (U.S. Patent Appn. No. 20060088510).

In another embodiment, the invention provides an isolated CCL20 locked dimer polypeptide as described above. By "isolated" we mean a nucleic acid sequence that is identified and separated from at least one component or contaminant with which it is ordinarily associated. An isolated nucleic acid is present in a form or setting that is different from that in which it is found in nature. In contrast, non-isolated nucleic acids such as DNA and RNA are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, an isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

The CCL20 locked dimer polypeptide of the present invention can be prepared by standard techniques known in the art. The peptide component of CCL20 is composed, at least in part, of a peptide, which can be synthesized using standard techniques such as those described in Bodansky, M. Principles of Peptide Synthesis, Springer Verlag, Berlin (1993) and Grant, G. A. (ed.). Synthetic Peptides: A User's Guide, W. H. Freeman and Company, New York (1992). Automated peptide synthesizers are commercially available (e.g., Advanced ChemTech Model 396; Milligen/Biosearch 9600). Additionally, one or more modulating groups can be attached by standard methods, such as by using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine residue) or other suitable reactive group on an amino acid side chain (see e.g., Greene, T. W. and Wuts, P. G. M. Protective Groups in Organic Synthesis, John Wiley and Sons, Inc., New York (1991)).

Peptides of the invention may be chemically synthesized using standard techniques such as those described in Bodansky, M. Principles of Peptide Synthesis, Springer Verlag, Berlin (1993) and Grant, G. A. (ed.). Synthetic Peptides: A User's Guide, W. H. Freeman and Company, New York, (1992) (all of which are incorporated herein by reference).

In another aspect of the invention, peptides may be prepared according to standard recombinant DNA techniques using a nucleic acid molecule encoding the peptide. A nucleotide sequence encoding the peptide can be determined using the genetic code and an oligonucleotide molecule having this nucleotide sequence can be synthesized by standard DNA synthesis methods (e.g., using an automated DNA synthesizer). Alternatively, a DNA molecule encoding a peptide compound can be derived from the natural precursor protein gene or cDNA (e.g., using the polymerase chain reaction (PCR) and/or restriction enzyme digestion) according to standard molecular biology techniques.

In other embodiments of the present invention, the invention provides vectors comprising DNA encoding any of the herein described polypeptides. Host cell comprising any such vector are also provided. By way of example, the host cells may be CHO cells, *E. coli*, SP9 insect cells or yeast. A process for producing any of the herein described polypeptides is further provided and comprises culturing host cells comprising a vector that encodes the polypeptide under conditions suitable for expression of the desired polypeptide and recovering the desired polypeptide from the cell culture.

CCL20 Locked Dimer Polypeptide Pharmaceutical Compositions.

In another embodiment, the invention provides a composition comprising a substantially pure CCL20 locked dimer polypeptide of the present invention, and a pharmaceutically acceptable carrier. By "pharmaceutically acceptable carrier" we mean any and all solvents, dispersion media, coatings, antibacterial and antifungal agents, isotonic and absorption delaying agents, and the like that are physiologically compatible. In one embodiment, the carrier may be suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, membrane nanoparticle or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, such as, monostearate salts and gelatin.

Moreover, the CCL20 locked dimer polypeptide of the present invention can be administered in a time-release formulation, such as in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. CXCR4 antagonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. The CCL20 locked dimer polypeptide of the present invention also may be formulated with one or more additional compounds that enhance the solubility of the CCL20 locked dimer polypeptide.

Administration.

The CCL20 locked dimer polypeptide of the present invention, optionally comprising other pharmaceutically active compounds, can be administered to a patient orally, rectally, parenterally, (e.g., intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the CCL20 locked dimer of the invention combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (e.g., propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the CCL20 locked dimer polypeptide is provided in dry (i.e., powder or granular) form for reconstitution with a suitable vehicle (e.g., sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

The CCL20 locked dimer polypeptide of the present invention may also contain adjuvants such as suspending, preserving, wetting, emulsifying, and/or dispersing agents, including, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, such as aluminum monostearate and/or gelatin.

Dosage forms can include solid or injectable implants or depots. In preferred embodiments, the implant comprises an effective amount of the $\alpha_2$ locked dimer polypeptide and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(ε-caprolactone), a polyanhydride, a poly(beta-hydroxy butyrate), a poly(ortho ester) and a polyphosphazene. In other embodiments, the implant comprises an effective amount of CCL20 locked dimer polypeptide and a silastic polymer. The implant provides the release of an effective amount of CCL20 locked dimer polypeptide for an extended period ranging from about one week to several years.

Solid dosage forms for oral administration include capsules, tablets, powders, and granules. In such solid dosage forms, the CCL20 locked dimer polypeptide is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Tablets may be manufactured with pharmaceutically acceptable excipients such as inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Dose Requirements.

In particular embodiments, a preferred range for therapeutically or prophylactically effective amounts of CCL20 locked dimer polypeptide may be 0.1 nM-0.1M, particularly 0.1 nM-0.05M, more particularly 0.05 nM-15 µM and most particularly 0.01 nM-10 It is to be noted that dosage values may vary with the severity of the condition to be alleviated, especially with multiple sclerosis. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The amount of CCL20 locked dimer polypeptide in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such as active compound for the treatment of sensitivity in individuals.

Methods of Use.

The invention also provides corresponding methods of use, including methods of medical treatment, in which a therapeutically effective dose of a CCL20 locked dimer polypeptide, preferably wherein the dimer comprises at least one monomer having the amino acid sequence according to SEQ ID NO:1, is administered in a pharmacologically acceptable formulation. Accordingly, the invention also provides therapeutic compositions comprising a CCL20 locked dimer polypeptide and a pharmacologically acceptable excipient or carrier, as described above. The therapeutic composition may advantageously be soluble in an aqueous solution at a physiologically acceptable pH.

In one embodiment, the invention provides a method of treating psoriasis, the method comprising administering a therapeutically effective amount of a composition comprising a CCL20 locked dimer polypeptide to a subject having or at risk of having psoriasis.

By "psoriasis" or "psoriasis vulgaris" we mean the common, chronic, relapsing or remitting, immune-mediated systemic disease characterized by skin lesions including red, scaly patches, papules, and plaques, which usually itch. The skin lesions seen in psoriasis may vary in severity from minor localized patches to complete body coverage. The five main types of psoriasis are plaque, guttate, inverse, pustular, and erythrodermic. Plaque psoriasis, the most common form, typically manifests as red and white scaly patches on the top layer of the skin. Skin cells rapidly accumulate at these plaque sites and create a silvery-white appearance.

In one embodiment, the invention provides a method of treating an inflammatory disease, the method comprising administering a therapeutically effective amount of a composition comprising a CCL20 locked dimer polypeptide to a subject having or at risk of having an inflammatory disease a therapeutically effective amount of a composition comprising a CCL20 locked dimer polypeptide.

By "inflammatory disease" we mean any chronic or acute condition caused by inflammation, including, for example, eczema, periodontitis, atherosclerosis, and rheumatoid arthritis. By "inflammation" we mean the complex biological response of vascular tissues to harmful stimuli, such as pathogens, damaged cells, or irritants. It is a protective attempt by the organism to remove the injurious stimuli as well as initiate the healing process for the tissue. For instance, the composition and methods of the present invention can be utilized to treat inflammation associated with an allergic disease such as asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy; a neurodegenerative disease; a cardiovascular disease; a gastrointestinal disease; septic shock; anaphylactic shock; toxic shock syndrome; cachexia; necrosis; gangrene; menstruation; an ulcer such as a skin ulcer, a bed sore, a gastric ulcer, a peptic ulcer, a buccal ulcer, a nasopharyngeal ulcer, an esophageal ulcer, a duodenal ulcer and a gastrointestinal ulcer; an injury such as an abrasion, a bruise, a cut, a puncture wound, a laceration, an impact wound, a concussion, a contusion, a thermal burn, frostbite, a chemical burn, a sunburn, a desiccation, a radiation burn, a radioactivity burn, smoke inhalation, a torn muscle, a pulled muscle, a torn tendon, a pulled tendon, a pulled ligament, a torn ligament, a hyperextension, a torn cartilage, a bone fracture, a pinched nerve and a gunshot wound; a musculo-skeletal inflammation such as a muscle inflammation, myositis, a tendon inflammation, tendinitis, a ligament inflammation, a cartilage inflammation, a joint inflammation, a synovial inflammation, carpal tunnel syndrome and a bone inflammation. CCL20 has been implicated in a variety of cancers and particularly is involved in the development of colorectal cancer.

In one embodiment, the invention provides a method of treating an autoimmune disease, the method comprising administering a therapeutically effective amount of a composition comprising a CCL20 locked dimer polypeptide to a subject having or at risk of having an autoimmune disease a therapeutically effective amount of a composition comprising a CCL20 locked dimer polypeptide.

By "autoimmune disease" we mean illnesses generally understood to be caused by the over-production of cytokines, lymphotoxins and antibodies by white blood cells, including in particular T-cells. Such autoimmune diseases include but are not limited to Multiple Sclerosis (MS), Guillain-Barre Syndrome, Amyotrophic Lateral Sclerosis, Parkinson's disease, Alzheimer's disease, Diabetes Type I, gout, lupus, and any other human illness that T-cells play a major role in, such as tissue graft rejection. In addition, diseases involving the degradation of extra-cellular matrix include, but are not limited to, psoriatic arthritis, juvenile arthritis, early arthritis, reactive arthritis, osteoarthritis, ankylosing spondylitis. osteoporosis, muscular skeletal diseases like tendonitis and periodontal disease, cancer metastasis, airway diseases (COPD, asthma or other reactive airways disease), renal and liver fibrosis, cardio-vascular diseases like atherosclerosis and heart failure, and neurological diseases like neuroinflammation and multiple sclerosis. Diseases involving primarily joint degeneration include, but are not limited to, rheumatoid arthritis, psoriatic arthritis, juvenile arthritis, early arthritis, reactive arthritis, osteoarthritis, ankylosing spondylitis. Diseases involving the eye include, but are not limited to autoimmune uveitis and uveoconjunctivitis and dry eye syndrome. Diseases involving post-infections complications of viral or bacterial diseases such as glomerulonephritis, vasculitis, meningoencephalitis. Diseases involving the gastrointestinal system include but are not limited to inflammatory bowel diseases.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex.

By "treating" we mean the management and care of a subject for the purpose of combating the disease, condition, or disorder. The terms embrace both preventative, i.e., prophylactic, and palliative treatments. Treating includes the administration of a compound of the present invention to prevent, ameliorate and/or improve the onset of the symptoms or complications, alleviating the symptoms or complications, or eliminating the disease, condition, or disorder.

By "ameliorate", "amelioration", "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the locked dimer of the present invention, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the locked dimer of the present invention is administered to a subject or is used in an assay or other method described herein or a cited reference, e.g., within about 1 hour of the administration or use of the locked dimer of the present invention to about 3, 6, 9 months or more after a subject(s) has received the locked dimer of the present invention.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the locked dimer of the present invention, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the locked dimer of the present invention is administered to a subject or is used in an assay or other method described herein or a cited reference, e.g., within about 1 hour of the administration or use of the locked dimer of the present invention to about 3, 6, 9 months or more after a subject(s) has received the locked dimer of the present invention.

By "administering" we mean any means for introducing the CCL20 locked dimer polypeptide of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection.

By "therapeutically effective amount" we mean an amount effective, at dosages and for periods of time necessary, to achieve the desired therapeutic result, such as reduction or reversal of angiogenesis in the case of cancers, or reduction or inhibition of T-cells in autoimmune diseases. A therapeutically effective amount of the CCL20 locked dimer polypeptide may vary according to factors such as the disease state, age, sex, and weight of the subject, and the ability of the CCL20 locked dimer polypeptide to elicit a desired response in the subject. Dosage regimens may be adjusted to provide the optimum therapeutic response. A therapeutically effective amount is also one in which any toxic or detrimental effects of the CCL20 locked dimer polypeptide are outweighed by the therapeutically beneficial effects.

A "prophylactically effective amount" refers to an amount effective, at dosages and for periods of time necessary, to achieve the desired prophylactic result, such as preventing or inhibiting the rate of metastasis of a tumor or the onset of bouts or episodes of multiple sclerosis. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

Kits.

In another embodiment, the present invention provides a kit comprising a pharmaceutical composition according to the present invention and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention may also further comprise a delivery device for delivering the composition to a subject. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container.

Sequence Listing: The following are polypeptide sequences of suitable monomers used in the present invention.

(S64C)
SEQ ID NO: 1
(ASNFDCCLGYTDRILHPKFIVGFTRQLANEGCDINAIIFHTKKKLSVCA

NPKQTWVKYIVRLLCKKVKNM)

(V21C/T24C)
SEQ ID NO: 2
(ASNFDCCLGYTDRILHPKFICGFCRQLANEGCDINAIIFHTKKKLSVCA

NPKQTWVKYIVRLLSKKVKNM)

(G22C/T24C)
SEQ ID NO: 3
(ASNFDCCLGYTDRILHPKFIVCFCRQLANEGCDINAIIFHTKKKLSVCA

NPKQTWVKYIVRLLSKKVKNM)

(F23C)
SEQ ID NO: 4
(ASNFDCCLGYTDRILHPKFIVGCTRQLANEGCDINAIIFHTKKKLSVCA

NPKQTWVKYIVRLLSKKVKNM)

(V60C)
SEQ ID NO: 5
(ASNFDCCLGYTDRILHPKFIVGFTRQLANEGCDINAIIFHTKKKLSVCA

NPKQTWVKYICRLLSKKVKNM)

(V67C)
SEQ ID NO: 6
(ASNFDCCLGYTDRILHPKFIVGFTRQLANEGCDINAIIFHTKKKLSVCA

NPKQTWVKYIVRLLSKKCKNM)

III. Examples

The following examples describing materials and methodology are offered for illustrative purposes only, and are not intended to limit the scope of the present invention.

Construction of the CCL20 S64C Variant.

Dimerization is essential for the in vivo function of chemokines and as a result engineered monomers and dimers of various CC and CXC chemokines have been used to probe their respective roles in chemokine signaling (Proudfoot et al., 2003). The CXC-type dimer observed in two different CCL20 X-ray crystal structures is unusual for a member of the CC chemokine family, and NMR studies indicate that CCL20 self-association is relatively weak and pH dependent (Chan et al., 2008). To probe the functional activity of the crystallographic CCL20 dimer, we designed a crosslinked dimer using Disulfide by Design to predict intermolecular disulfide links using one of the X-ray crystal structures (PDB code 2HCI) (Dombkowski, 2003). From visual inspection of a list of candidates, we generated two single-cysteine and three double-cysteine substitution CCL20 variants for experimental testing. These cysteine variants contained substitutions at the $1^{st}$ β-strand (V21C/T24C, G22C/T24C and F23C) and the α-helix (V60C/V67C and S64C). Each variant was purified, refolded, and analyzed by HPLC and MALDI-TOF mass spectrometry. Only one variant, CCL20 S64C, which is predicted to make a symmetrical, intermolecular disulfide bond between opposing α-helices (FIGS. 1A-B), yielded sufficient pure, folded protein suitable for further analysis.

Co-injection of CCL20 WT and S64C proteins onto reverse phase HPLC produced a chromatogram with two distinct peaks (FIG. 1C). Injection of CCL20 WT or CCL20 S64C alone revealed that the retention times for each protein matched those in the co-injection and that no monomeric species was observed in the dimer sample. Quadrupole-Orbitrap mass spectrometry was used to confirm the molecular weight of 16080.4 kDa for the disulfide-linked CCL20 variant (FIG. 1D). The 2D $^1$H-$^{15}$N heteronuclear single quantum coherence (HSQC) spectrum of CCL20 S64C shows 79 well-dispersed peaks consistent with a homogeneous, folded protein that is distinct from wild-type CCL20 (FIG. 1E). The oligomeric state of CCL20 S64C was confirmed by SDS-PAGE of disulfide-reduced and non-reduced samples, which migrated at ~10 and 20 kDa, respectively (FIG. 1E). Based on the biophysical data, we conclude that replacement of Ser 64 with cysteine yielded a disulfide-linked symmetric CCL20 homodimer.

In Vitro Testing of CCL20 S64C.

Some CXC chemokine dimers can bind and activate their receptors, but dimerization of CC chemokines typically blocks receptor binding, rendering them non-functional as GPCR agonists (Ravindran et al., 2013; Tan et al., 2012). We compared the CCR6 agonist activity of recombinant CCL20 WT and CCL20 S64C proteins in calcium flux and cell chemotaxis assays using transfected CCR6$^+$ Jurkat cells. Both molecules induced CCR6-mediated intracellular calcium flux at nanomolar concentrations with CCL20 S64C~9-fold less potent than the unmodified (FIG. 2A). In a filter-based migration assay, CCL20 induced CCR6$^+$ Jurkat cell migration with a typical biphasic concentration dependence and a maximal response observed at 100 nM ($EC_{50}$~15 nM) (FIG. 2B). In contrast, exposure to CCL20 S64C in the same assay produced no significant cell migration (FIG. 2B). These results suggest that the disulfide-linked CCL20 dimer retains the ability to bind CCR6 and induce G protein signaling but fails to stimulate other CCL20-induced signaling pathways required for cellular chemotaxis.

We monitored the effect of CCL20 S64C in blocking CCR6$^+$ Jurkat cell migration induced by 30 nM CCL20 WT. CCL20 S64C dose-dependently inhibited chemotaxis with an $IC_{50}$ 100 nM (FIG. 2C). CCL20 S64C also blocked chemotaxis in response to human beta defensin 2 (hBD2), another secreted protein that binds to CCR6 and promotes cell migration (FIG. 2D). Of note, CCL20 S64C did not inhibit THP-1 cell migration mediated by CXCR4 and CCR2, the cognate receptors for chemokines CXCL12 and CCL2, respectively. In the presence of 10 nM CXCL12 and 1 nM CCL2, the CCL20 S64C variant showed no inhibitory effects on THP-1 cell migration upon treatment with either chemokines, suggesting that CCL20 S64C selectively blocked CCR6-mediated chemotaxis. Taken together, these results indicated that CCL20 S64C inhibits CCL20-induced chemotaxis by binding specifically to the CCR6 receptor rather than interacting directly with CCL20 or by blocking other downstream cell migration signaling pathways.

Anti-Inflammatory Activity of CCL20 S64C in IL-23-Induced Psoriasis.

Based on its ability to block CCL20-mediated cell migration in vitro in a CCR6-specific manner, we speculated that CCL20 S64C could attenuate the inflammation associated with psoriasiform dermatitis in vivo. To identify a potential therapeutic role of CCL20 S64C in vivo, we used an IL-23-induced model of psoriasiform dermatitis. Exposure to IL-23 is known to drive T cells toward Th17 differentiation and to stimulate migration of other inflammatory cells to the epidermis, resulting in dermal inflammation that can be measured with a micrometer over time (Hedrick et al., 2009). We injected IL-23 with CCL20 S64C, IL-23 with CCL20 WT or IL-23 alone into the ear skin of mice and measured ear thickness every other day for five days. As expected, mice injected with IL-23 and CCL20 WT or IL-23 alone displayed reproducible ear swelling. The addition of CCL20 S64C with IL-23 resulted in a significant reduction in ear thickness as compared to the other groups (FIG. 3A). The lack of prevention by equimolar amounts of CCL20 WT indicates that the observed effects are due to the disulfide-linked dimeric conformation of CCL20 S64C and not to increased levels of CCL20 in general.

In addition to measurement of ear thickening, we examined the effect of CCL20 S64C in the IL-23 model at the histological level. Hematoxylin and eosin (H&E) staining was used to characterize immune cell infiltration to the epidermis. Injection with IL23 alone (or with CCL20 WT protein) resulted in marked epidermal hyperplasia and a dense mixture of mononuclear inflammatory infiltrate (FIG. 3B). In contrast, mice treated with IL-23 and CCL20 S64C showed reduced epidermal hyperplasia and decreased inflammatory cell infiltration, which was comparable to PBS control (FIG. 3B). Thus, CCL20 S64C treatment markedly reduced epidermal hyperplasia and dermal inflammation, two key signatures of psoriasiform dermatitis.

Next, we evaluated the specific effects of CCL20 treatments on T cell trafficking and biomarker expression in the epidermis. Epidermal cell suspensions were stained with monoclonal antibodies against the γδ-T cell receptor. In murine skin, two distinct populations of γδ-T cells that express high or low γδ-TCR, are recognized in uninflamed skin, where epidermal γδ-high T cells (also called dendritic epidermal T cells) are present in much higher numbers compared to γδ-low T cells (Girardi, 2006). In IL-23 treated skin, γδ-low T cells are markedly increased in the dermis and epidermis (Mabuchi et al., 2011). Furthermore, the recruited GDL T cells express high levels of IL-17A and IL-22, which are suggestive of Th17 differentiation. Similar to previous reports, the IL-23 alone treated mice showed an increase in epidermal GDL T cell populations as compared to the PBS control ($p<0.05$) (FIGS. 3C and 3E). When 100 nM CCL20WT was injected into the ear, no significant reduction in GDL T cell populations was observed. Remarkably, CCL20 S64C-treated mice showed a significant lack of a GDL T cell population in the epidermis (FIGS. 3C and 3E). These results confirmed our hypothesis that CCL20 S64C, but not wild-type CCL20, can block the trafficking of GDL T cells to the epidermis.

To further examine psoriasis biomarker expression levels, we performed RT-PCR analysis of IL-17A and IL-22, which are known to be elevated with the increase of GDL T cells (Sutton et al., 2009). Epidermal cell suspensions from ears treated with CCL20 S64C showed a significant reduction in the expression of IL-22 and IL-17A mRNA compared with IL-23 alone treated ears (FIG. 3F). However, epidermal cells from ears treated with wild-type CCL20 exhibited higher IL-22 and IL-17A mRNA levels that were comparable to the IL-23 alone treatments. Thus, CCL20 S64C blocked the accumulation of GDL T cells in the epidermis and reduced the expression of IL-22 and IL-17A mRNA in the epidermis of treated mice.

Some locked chemokine dimers, while adopting the proper tertiary fold, cannot bind their cognate GPCRs, as in the case of CCL2 which loses its ability to bind to CCR2 as a disulfide-trapped dimer (Tan et al., 2012). In contrast, the CXCL1 preferential dimer maintains full agonist ability as a CXC dimer (Ravindran et al., 2013). Our engineered variant is the first disulfide linked CCL20 dimer that is able to interact with CCR6 and trigger intracellular calcium release, albeit with nearly ten-fold weaker potency. Chan et. al. performed molecular dynamics simulations on the dimeric crystal structures and the monomeric NMR structure of CCL20 and found that the receptor binding groove formed by the N-loop and $3^{rd}$ B-strand is ~1 Å narrower in the dimer compared to the monomer. The narrowed groove of the dimer could produce less favorable interactions between chemokine and receptor and explain the decreased potency of the CCL20 S64C dimer. Chan et. al. and others have also noted that the CCL20 crystal structure (2HCI) shows residues of the chemokine N-terminus on one monomer (Ser3 and Asn4) making contacts on the opposing monomer (Lys43). The CCL20 S64C variant would most likely favor these interactions due to the locked state and may position the chemokine N-terminus in a different orientation at the orthosteric pocket of CCR6, leading to oligomer-specific signaling. More structural studies of wild-type CCL20 and the S64C variant are needed to determine the key interactions between CCL20 and CCR6 that impart the observed oligomeric differences.

In this study, we demonstrated that the CCL20 S64C variant prevented psoriasiform dermatitis and blocked recruitment of GDL T cells to the epidermis, raising the possibility that neutralizing the CCL20/CCR6 pathway may be therapeutically helpful in human psoriatic diseases. Indeed, recent human clinical data support the importance of CCR6 and GDL T cells in psoriasis. Initial work characterized CCL20 as the most highly upregulated chemokine in human psoriatic legions (Homey et al., 2000). Additionally, it has been reported that psoriatic patients have increased circulating levels of IL-17A$^+$ CCR6$^+$ cells in the blood and that IL-17A$^+$ CCR6$^+$ γδ T cells are present in greater numbers in psoriatic lesions compared to normal skin (Kagami et al., 2010; Laggner et al., 2011). The role of CCR6 in activated T cell function highlights the therapeutic potential of the CCL20 S64C variant in not only psoriasis but also other diseases that utilize Th17-mediated pathways.

The CCL20 locked dimer would be administered at regular intervals to a patient with active psoriatic skin lesions by a systemic route, including intravenous administration.

CCL20 Locked Dimer Plasmid Generation.

The CCL20S64C plasmid was generated by site-directed mutagenesis using complimentary primers using the Quik-Cange Site-Directed Mutagenesis Kit (Stratagene). Mutant plasmid confirmed by DNA sequencing.

Protein Purification.

CCL20S64C, CCL20WT and hBD2 proteins were expressed and purified as previously described (Takekoshi et al., 2012). Briefly, *E. coli* cells were lysed by French Press and centrifuged for 20 minutes at 15,000 rpm. The insoluble fraction was resuspended in a 6M guanidine buffer and nickel chromatography purified. CCL20S64C elutions were pooled and refolded drop-wise into a 20 mM cysteine, 0.5 mM cystine, 100 mM Tris, (pH 8.0) buffer. CCL20WT and hBD2 elutions were refolded in a 10 mM cysteine, 0.5 mM cystine, 100 mM Tris (pH 8.0) buffer. Refolded CCL20 and hBD2 proteins were cleaved with recombinant ULP1 and the SUMO-6×HIS tag and was separated from the recombinant protein by cation exchange chromatography. After exchange chromatography, elutions were HPLC purified and lyophilized. Purity and molecular weights were confirmed by SDS-PAGE and MALDI-TOF spectrometry.

HPLC Chromatography.

Approximately 100 μg of recombinant CCL20S64C and CCL20WT proteins were resuspended in $H_2O$ and injected on a Shimadzu HPLC equipped with C18 column (Vydac). A 50-80% gradient of 70% acetonitrile (Sigma) and 0.1% TFA (Sigma) was used to elute proteins.

Mass Spectrometry.

Purified CCL20S64C was diluted to 1 μM in 70% acetonitrile containing 0.1% formic acid. Protein was analyzed by direct infusion using a Q Exactive™ Hybrid Quadrupole-Orbitrap mass spectrometer (ThermoFisher Scientific). Analysis was performed with a resolving power set to 140,000. Data were deconvoluted and deisotoped using Xtract and Xcalibur™ in QualBrowser (ThermoFisher Scientific).

Reduced/Oxidized SDS-PAGE.

Approximately 3 μg of CCL20S64C or CCL20WT was resuspended in a SDS buffer in either the absence or presence of β-mercaptoethanol.

NMR Spectroscopy.

[U-$^{15}$N]-CCL20S64C and CCL20WT were resuspended in $H_2O$ and diluted to 50 μM in a 25 mM deuterated MES (pH 6.8), 10% (v/v) $D_2O$ and 0.02% (w/v) $NaN_3$ buffer. $^1$H-$^{15}$N Heteronuclear Single Quantum Coherence experiments were performed on a Bruker Avance 500 MHz spectrometer equipped with a TCI cryoprobe at 298K.

Calcium Flux Assay.

Transfected CCR6$^+$ Jurkat cells were washed twice in a Hanks buffered saline solution (HBSS), 25 mM HEPES (pH 7.4) and 0.2% (w/v) BSA buffer and $2\times10^5$ cells/well were incubated with FLIPR Calcium 4 dye at 37° C., 5% $CO_2$ for 1 hour in a 384-well HTS plate (Greiner bio-one). Chemokine dilutions were made in buffer and added to the plate after a 20 s baseline reading. Fluorescence at 515 nm was observed using a Flexstation 3 (Molecular Devices) for an additional 80 seconds. Total fluorescent signal was measured and four replicates from two separate days were measured and are presented as the mean±SEM. $EC_{50}$ values were calculated through non-linear fitting to a four-parameter function.

Chemotaxis Assay.

Chemokine and hBD2 dilutions were prepared as indicated in a RPMI 1640, 25 mM HEPES (pH 7.4) and 0.2% BSA buffer and added to the lower well of a Corning HTS Transwell®-96 well plate (5 μm pore size). Transfected CCR6$^+$ Jurkat cells were washed in buffer and $3.6\times10^4$ cells were added to the upper well and allowed to incubate at 37° C., 5% $CO_2$ for 2 hours. Migrated cells in the lower well were quantitated on a BD™ LSR II flow cytometer. Total cell number is the average of four replicates from two separate days and presented as the mean±SEM. Significance determined by a two-tailed, unpaired Student's T-test.

Mice.

C57BL/6J mice were purchased from The Jackson Laboratory. All mice were used at 8-12 weeks of age. Animal protocols were approved by the Animal Care and Use Committees at the Medical College of Wisconsin.

Cytokine Injections into Mouse Ears.

Intradermal injections of 500 ng recombinant mouse IL-23 (BioLegend) in 20 μl PBS were performed into both ears of anesthetized mice every other day for 6 days as described previously (Mabuchi et al., 2011). In a similar manner, we administered an intradermal injection of 20 μl PBS containing 32 ng (0.1 μM) recombinant CCL20S64C mixed with 500 ng recombinant mouse IL-23, 20 μl PBS containing 16 ng (0.1 μM) recombinant CCL20WT mixed with 500 ng recombinant mouse IL-23. Ear thickness was measured before every injection using a dial thickness gauge (Ozaki).

Processing of Epidermal Cells from Mouse Ears.

After recovery of mouse ears, skin sheets were separated from cartilage and incubated in PBS containing 0.5% trypsin (Affymetrix) for 40 minutes at 37 degrees Celsius to separate epidermal sheets from dermal sheets. To obtain cell suspensions, epidermal sheets were treated in DMEM (Invitrogen) containing 0.05% DNase I (Sigma-Aldrich) as described (Mabuchi et al., 2013).

Flow Cytometry.

Anti mouse γδ-TCR (clone: GL3) were purchased from BioLegend. Cells from mouse epidermis were examined using a Acuri C6 (BD Biosciences). Flow cytometric data were analyzed using FlowJo version 10.0.7 software (Tree Star).

Quantitative Real-Time PCR (RT-PCR).

Extraction of RNA and subsequent analysis of mRNA expression of indicated cytokines from epidermis was performed as described (Mabuchi et al., 2011). In brief, total RNA of mouse epidermis was prepared using an RNeasy Fibrous Tissue Kit (Qiagen) according to the manufacturer's instructions and RT-PCR was performed via StepOnePlus Real-Time PCR System (Applied Biosystems).

Histopathological Analysis.

Skin specimens were sampled, fixed with 10% formaldehyde, and embedded in paraffin. Those tissues were sectioned at 4 μm thickness, and deparaffinized sections were stained with H&E.

Statistics.

All data are expressed as mean±SEM. Calcium flux and chemotaxis $EC_{50}$ and $IC_{50}$ values were analyzed using ProFit 6 and in house scripts. In vivo data was analyzed using GraphPad Prism version 6 (GraphPad Software). Simple comparisons of means and SEM of data were made by using two-sided Student's t-test and multiple comparisons were made by using Tukey's test. A P-value less than 0.05 is considered statistically significant.

Using the CCL20 Locked Dimer in the Treatment of Inflammatory Diseases.

In one embodiment, the locked dimer of the present invention may be used as an agonist or antagonist in combination with other known anti-inflammatory therapies. By "agonist" we mean a ligand that stimulates the receptor the ligand binds to in the broadest sense. An "agonist" or an "antagonist" is a compound or composition that, respectively, either detectably increases or decreases the activity of a receptor, an enzyme or another biological molecule, which can lead to increased or decreased transcription or mRNA levels of a regulated gene or to another measurable effect such as altered level of activity of the gene product or protein. The increase or decrease in a receptor's or enzyme's activity will be an increase or a decrease of at least about 5%, 10%, 20%, 30%, 40%, 50%, 60%, 70%, 80%, 90%, 95% or a range about between any two of these values, for one or more measurable activities. Receptors, their accessory factors and associated transcription factors can modulate transcription of their target gene(s) by detectably increasing or decreasing transcription or mRNA levels. Biological activities of receptors may also include modulating biological responses such as signal transduction within a cell or ion flux, e.g., sodium, potassium or calcium, across cell or organelle membranes, e.g., across mitochondria.

The anti-inflammatory activity of the combination therapies of invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993), incorporated herein by reference in its entirety.

The anti-inflammatory activity of the invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," Inflammation, 24(2): 141-155, (2000). Also commonly used are zymosan-induced inflammation animal models as known and described in the art.

The anti-inflammatory activity of the invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" Proc. Soc. Exp. Biol Med. 111, 544-547, (1962). This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group. Additionally, animal models for inflammatory bowel disease can also be used to assess the efficacy of the combination therapies of invention.

Animal models for asthma can also be used to assess the efficacy of the combination therapies of invention. An example of one such model is the murine adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (Cohn et al., 1997, J. Exp. Med. 186, 1737-1747).

Using the CCL20 Locked Dimer in the Treatment of Auto-Immune Diseases.

The CCL20 locked dimer of the present invention would be beneficial in autoimmune disease in which expression of CCR6 is a prominent feature of the T cells infiltrating the affected tissue. Treatment would consist of administering the drug systemically to the patient with active disease. Animal models for autoimmune disorders can also be used to assess the efficacy of the combination therapies of invention. Animal models for autoimmune disorders such as type 1 diabetes, thyroid autoimmunity, systemic lupus eruthematosus, and glomerulonephritis have been developed. Further, any assays known to those skilled in the art can be used to evaluate the prophylactic and/or therapeutic utility of the combinatorial therapies disclosed herein for autoimmune and/or inflammatory diseases.

Animal models for autoimmune and/or intestinal inflammation can also be used to test the efficacy of the combination therapies of the invention. An example of one such model is the murine dextran sodium sulfate colitis model as described in Wirtz S. et al., "Chemically induced mouse models of intestinal inflammations" Nature Protocols 2, 541-546, (2007).

X-Ray Crystal Structure of CCL20 S64C

Some chemokines form higher order structures displaying characteristic dimer features shared with other chemokine classes. To validate CCL20's CXC-type dimer conformation in solution, we solved the X-ray crystal structure of CCL20 S64C through molecular replacement. The protein crystallized in an ammonium acetate buffer and packed in the hexagonal space group ($P6_1$) to give a final structure resolution of 2.0 Å. Two CCL20 molecules are in the asymmetrical unit, forming the expected CXC-type dimer. The monomer subunit structure is similar to other previously solved chemokines, where an unstructured N-terminal region followed by two intramolecular disulfide bonds, an N-loop region, and three β-strands. The C-terminal α-helices in both subunits make contacts with the opposing subunits 30's loop/β-strands and are connected through an intermolecular disulfide bond, with well-defined electron density across the entire bond (FIG. 4a, b).

The locked dimer structure shows high similarity to other CCL20 structures. The N-terminus is extremely flexible, with observed electron densities beginning at D5, the amino acid preceding the first disulfide bind, in both subunits. The structure has full electron density through M70 in both monomer chains due to the hydrogen bonding between the backbone oxygen of M70 and the of K52; the terminal residue is not observed in any other CCL20 crystal structure. CCL20 S64C self-associates along the β1-strands and forms a characteristic hydrogen-bonding pattern between backbone atoms of V21, F23 and R25 (FIG. 4c). Additionally, the dimer is stabilized by hydrophobic contacts between each α-helix and the opposing subunit's β-strands, as seen for V67 in monomer A and F23 of monomer B. Along with van der Waal contacts, hydrogen bonds between K57 and the opposing subunit's V67 backbone oxygen stabilize the dimer and makes additional contributions to the stabilization of the C-terminus.

Recognition of monomeric and some dimeric chemokines is facilitated through the recognition of a conserved N-loop/β3-strand motif on the chemokine surface (Blanpain et al., 2003; Baly et al., 1998; Bondue et al., 2001). FIG. 4d shows an overlay of this binding cleft in the CCL20 locked dimer and monomeric CCL20 (PDB ID=2JYO). The CCL20 locked dimer adopts a similar pocket conformation as the monomer, with an RMSD=0.97 Å for the Ca atoms for residues 10-50. Additionally, the side chains of monomeric and dimeric R13, F19, and V47 adopt similar orientations in the pocket, with the R13 amino group pointed into the pocket and in close proximity to V47. No symmetry mates or other protein-protein interactions are found near this pocket in the dimer X-ray structure.

CCL20 S64C is a Biased Agonist for CCR6.

Some CXC chemokine dimers can bind and activate their receptors, but dimerization of CC chemokines typically blocks binding, rendering them non-functional as GPCR agonists (Tan et al., 2012; Ravindran et al., 2013). In order to test if the dimer has biological relevance, we compared the locked dimer and wild type CCL20 for their ability to bind and activate CCR6. Radioligand displacement of $I^{125}$-CCL20 WT on CCR6$^+$ COS7 cells showed a ten-fold change in affinity between CCL20 WT and CCL20 S64C with $K_d$ values of 7.6 nM and 74.4 nM, respectively (FIG. 5a). Next, we evaluated the dimer's ability to activate CCR6 relative to CCL20 WT by measuring intracellular calcium release. On CCR6$^+$ Jurkat cells, both molecules induced CCR6-mediated calcium flux at nanomolar concentrations with CCL20 S64C~9-fold less potent than the unmodified (FIG. 5b). As a corollary to endoplasmic reticulum release of calcium and specific for association of the $G_{\alpha i}$ subunit with CCR6, $IP_3$ accumulation in COS-7 cells transfected with the Gqi4myr chimera G protein was measured (Rosenkilde et al., 2006). Dose-dependent administration of CCL20 WT and CCL20 S64C on COS-7 cells generated CCR6-mediated $IP_3$ accumulation with $EC_{50}$ values of 0.4 nM and 41.3 nM, respectively. In both assays evaluating G protein signaling, the CCL20 S64C retains the ability to activate CCR6 (FIG. 5c).

Upon agonist activation of chemokine receptors, G protein receptor kinases (GRKS) phosphorylate the GPCR cytoplasmic tail and recruit multiple β-arrestin isotypes to the intracellular face of the receptor (Aramori et al., 1997). We tested the dimer's ability to recruit β-arrestin-2 using a β-galactosidase luminescence assay on transfected U2OS cells (FIG. 5d). β-arrestin-2 recruitment to CCR6 was measured in response to CCL20 WT and CCL20 S64C and produced $EC_{50}$ values of 1.1 nM and 86.2 nM, respectively.

We also evaluated CCR6 internalization in response to CCL20 WT and CCL20 S64C. Jurkat cells were incubated with 70 and 700 nM of each protein for 30 mins and CCR6 expression at the cell surface was quantified by flow cytometry. When treated with CCL20 S64C concentrations (700 nM) equal to or above the calcium flux and β-arrestin-2 recruitment $EC_{50}$ values, no significant CCR6 internalization was observed (FIG. 5e). In contrast, CCL20 WT significantly reduced CCR6 surface expression in a concentration-dependent manner. Taken together, the selective activation of some but not all receptor mediated signaling pathways, classifies CCL20 S64C as a biased agonist for CCR6.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference for all purposes. It is understood that the invention is not confined to the specific reagents, formulations, reaction conditions, etc., herein illustrated and described, but embraces such modified forms thereof as come within the scope of the following claims.

REFERENCES

Aramori, I. et al. 1997. *The EMBO journal*. 16: 4606-4616.
Baba, M. et al. 1997. *The Journal of biological chemistry*. 272:14893-14898.
Baly, D. L. et al. 1998. *Journal of immunology*. 161: 4944-4949.
Blanpain, C. et al. 2003. *The Journal of biological chemistry*. 278: 5179-5187.
Bondue, A. et al. 2001. *Proceedings of the National Academy of Sciences of the United States of America*. 98: 13722-13727.
Campanella, G. S. et al. 2006. *Journal of immunology*. 177:6991-6998.
Chan, D. I. et al. 2008. *Antimicrobial agents and chemotherapy*. 52:883-894.
Crump, M. P. et al. 1997. *The EMBO journal*. 16:6996-7007.
Dombkowski, A. A. 2003. *Bioinformatics*. 19:1852-1853.
Drury, L. J. et al. 2011. *Proc. of the Natl Acad. of Sciences*. 108:17655-17660.

Girardi, M. 2006. *The Journal of investigative dermatology.* 126:25-31.
Hassan, S. et al. 2011. *Int. of cancer. Journal international du cancer.* 129:225-232.
Hedrick, M. N. et al. 2009. *The Journal of clinical investigation.* 119:2317-2329.
Homey, B. et al. 2000. *J. of immunology.* 164:6621-6632.
Hoover, D. M. et al. 2002. *The Journal of biological chemistry.* 277:37647-37654.
Jansma, A. et al. 2009. *Chapter 2. Methods in enzymology.* 461:31-50.
Kagami, S. et al. 2010. *The Journal of investigative dermatology.* 130:1373-1383.
Kufareva, I. et al. 2014. *Proc. Natl Academy of Sciences.* 111:E5363-5372.
Kurd, S. K. et al. 2009. *American Academy of Dermatology.* 60:218-224.
Laggner, U et al. 2011. *Journal of immunology.* 187:2783-2793.
Langley, R. G. et al. 2014. *The New England journal of medicine.* 371:326-338.
Liao, F. et al. 1999. *Journal of immunology.* 162:186-194.
Mabuchi, T. et al. 2011. *Journal of immunology.* 187:5026-5031.
Malik, Z. A. et al. 2006. *Acta crystallographica.* 62:631-634.
Proudfoot, A. E. et al. 2003. *Proceedings of the National Academy of Sciences.* 100:1885-1890.
Ravindran, A. et al. 2013. *The Journal of biological chemistry.* 288:12244-12252.
Rodriguez-Frade, J. M. et al. 1999. *The Journal of cell biology.* 144:755-765.
Rosenkilde, M. M. et al. 2004. *The Journal of biological chemistry.* 279:3033-3041.
Rosenkilde, M. M. et al. 2006. *The Journal of biological chemistry.* 281: 13199-13208.
Sutton, C. E. et al. 2009. *Immunity.* 31:331-341.
Takekoshi, T et al. 2012. *Molecular cancer therapeutics.* 11:2516-2525.
Tan, J. H et al. 2012. *The Journal of biological chemistry.* 287:14692-14702.
Tan, J. H., et al. 2013. *The Journal of biological chemistry.* 288:10024-10034.
Veldkamp, C. T. et al. 2008. *Sci Signal.* 1:ra4.
Zidar, D. A. et al. 2009. *Proceedings of the National Academy of Sciences.* 106:9649-9654.

---

We claim:

1. A CCL20 locked dimer polypeptide, wherein the dimer comprises two monomers covalently linked together, wherein each monomer is an amino acid sequence comprising SEQ ID NO: 1.

2. A composition comprising the CCL20 locked dimer polypeptide of claim 1, and a pharmaceutically acceptable carrier or diluent.

3. The CCL20 dimer polypeptide of claim 1, wherein the covalent link is a disulfide bond.

4. A kit comprising a CCL20 locked dimer polypeptide wherein the dimer comprises covalently linked monomers wherein the amino acid sequence of each monomer comprises SEQ ID NO:1, a pharmaceutically acceptable carrier or diluents and instructional material.

* * * * *

UNITED STATES PATENT AND TRADEMARK OFFICE
CERTIFICATE OF CORRECTION

PATENT NO. : 10,738,095 B2
APPLICATION NO. : 15/579114
DATED : August 11, 2020
INVENTOR(S) : Brian F. Volkman et al.

It is certified that error appears in the above-identified patent and that said Letters Patent is hereby corrected as shown below:

In the Specification

Column 19, Line 60, "SUMO=6×HIS" should be --SUMO-6XHIS--.

Column 23, Line 30, "the of K52" should be --the Nζ of K52--.

Column 23, Line 38, "K57 and" should be --K57 Nζ and--.

Column 25, Line 3, "Int. of" should be --Int. J. of--.

Column 25, Line 16, "2009. American" should be --2009. J. American--.

Signed and Sealed this
Tenth Day of November, 2020

Andrei Iancu
*Director of the United States Patent and Trademark Office*

SEQUENCE LISTING

```
<160> NUMBER OF SEQ ID NOS: 7

<210> SEQ ID NO 1
<211> LENGTH: 70
<212> TYPE: PRT
<213> ORGANISM: Artificial Sequence
<220> FEATURE:
<223> OTHER INFORMATION: synthetic

<400> SEQUENCE: 1

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Cys
    50                  55                  60

Lys Lys Val Lys Asn Met
65                  70

<210> SEQ ID NO 2
<211> LENGTH: 70
<212> TYPE: PRT
<213> ORGANISM: Artificial Sequence
<220> FEATURE:
<223> OTHER INFORMATION: synthetic

<400> SEQUENCE: 2

Ala Ser Asn Phe Asp Cys Cys Leu Gly Tyr Thr Asp Arg Ile Leu His
1               5                   10                  15

Pro Lys Phe Ile Cys Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asn Met
```

<210> SEQ ID NO 3
<211> LENGTH: 70
<212> TYPE: PRT
<213> ORGANISM: Artificial Sequence
<220> FEATURE:
<223> OTHER INFORMATION: synthetic

<400> SEQUENCE: 3

```
Ala Ser Asn Phe Asp Cys Cys Leu Gly Tyr Thr Asp Arg Ile Leu His
1               5                   10                  15
Pro Lys Phe Ile Val Gly Phe Cys Arg Gln Leu Ala Asn Glu Gly Cys
            20                  25                  30
Asp Ile Asn Ala Ile Ile Phe His Thr Lys Lys Leu Ser Val Cys
        35                  40                  45
Ala Asn Pro Lys Gln Thr Trp Val Lys Tyr Ile Val Arg Leu Leu Ser
    50                  55                  60
Lys Lys Val Lys Asn Met
65                  70
```

<210> SEQ ID NO 4
<211> LENGTH: 70
<212> TYPE: PRT
<213> ORGANISM: Artificial Sequence
<220> FEATURE:
<223> OTHER INFORMATION: synthetic

<400> SEQUENCE: 4

```
Ala Ser Asn Phe Asp Cys Cys Leu Gly Tyr Thr Asp Arg Ile Leu His
1               5                   10                  15
Pro Lys Phe Ile Val Cys Phe Thr Arg Gln Leu Ala Asn Glu Gly Cys
            20                  25                  30
Asp Ile Asn Ala Ile Ile Phe His Thr Lys Lys Leu Ser Val Cys
        35                  40                  45
Ala Asn Pro Lys Gln Thr Trp Val Lys Tyr Ile Val Arg Leu Leu Ser
    50                  55                  60
Lys Lys Val Lys Asn Met
65                  70
```

<210> SEQ ID NO 5
<211> LENGTH: 70
<212> TYPE: PRT
<213> ORGANISM: Artificial Sequence
<220> FEATURE:
<223> OTHER INFORMATION: synthetic

<400> SEQUENCE: 5

```
Ala Ser Asn Phe Asp Cys Cys Leu Gly Tyr Thr Asp Arg Ile Leu His
1               5                   10                  15
Pro Lys Phe Ile Val Gly Cys Thr Arg Gln Leu Ala Asn Glu Gly Cys
            20                  25                  30
Asp Ile Asn Ala Ile Ile Phe His Thr Lys Lys Leu Ser Val Cys
        35                  40                  45
Ala Asn Pro Lys Gln Thr Trp Val Lys Tyr Ile Val Arg Leu Leu Ser
    50                  55                  60
Lys Lys Val Lys Asn Met
65                  70
```

<210> SEQ ID NO 6

```
<211> LENGTH: 70
<212> TYPE: PRT
<213> ORGANISM: Artificial Sequence
<220> FEATURE:
<223> OTHER INFORMATION: synthetic

<400> SEQUENCE: 6

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Cys Arg Leu Leu Ser
    50                  55                  60

Lys Lys Val Lys Asn Met
65                  70

<210> SEQ ID NO 7
<211> LENGTH: 70
<212> TYPE: PRT
<213> ORGANISM: Artificial Sequence
<220> FEATURE:
<223> OTHER INFORMATION: synthetic

<400> SEQUENCE: 7

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Cys Lys Asn Met
65                  70
```